US011484208B2

United States Patent
Addison

(10) Patent No.: US 11,484,208 B2
(45) Date of Patent: Nov. 1, 2022

(54) ATTACHED SENSOR ACTIVATION OF ADDITIONALLY-STREAMED PHYSIOLOGICAL PARAMETERS FROM NON-CONTACT MONITORING SYSTEMS AND ASSOCIATED DEVICES, SYSTEMS, AND METHODS

(71) Applicant: Covidien LP, Mansfield, MA (US)

(72) Inventor: Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/778,312

(22) Filed: Jan. 31, 2020

(65) Prior Publication Data

US 2021/0235992 A1 Aug. 5, 2021

(51) Int. Cl.
A61B 5/00 (2006.01)
G06T 7/55 (2017.01)
A61B 5/024 (2006.01)
A61B 5/08 (2006.01)
(Continued)

(52) U.S. Cl.
CPC ........ *A61B 5/0077* (2013.01); *A61B 5/02427* (2013.01); *A61B 5/0806* (2013.01); *A61B 5/14552* (2013.01); *A61B 5/742* (2013.01); *A61B 5/746* (2013.01); *G06T 7/0012* (2013.01); *G06T 7/55* (2017.01); *G06T 2207/10024* (2013.01); *G06T 2207/10028* (2013.01); *G06T 2207/10048* (2013.01); *G06T 2207/30196* (2013.01)

(58) Field of Classification Search
None
See application file for complete search history.

(56) References Cited

U.S. PATENT DOCUMENTS

| 5,107,845 A | 4/1992 | Guern et al. |
| 5,408,998 A | 4/1995 | Mersch |
| 5,704,367 A | 1/1998 | Ishikawa et al. |

(Continued)

FOREIGN PATENT DOCUMENTS

| CN | 106725410 A | 5/2017 |
| CN | 111728602 A | 10/2020 |

(Continued)

OTHER PUBLICATIONS

Mukherjee S, Dolui K, Datta SK. Patient health management system using e-health monitoring architecture. In 2014 IEEE international advance computing conference (IACC) Feb. 21, 2014 (pp. 400-405). IEEE. (Year: 2014).*

(Continued)

*Primary Examiner* — Clifford Hilaire
(74) *Attorney, Agent, or Firm* — Holzer Patel Drennan

(57) ABSTRACT

The present technology relates to the field of medical monitoring. Patient monitoring systems and associated devices, methods, and computer readable media are described. In some embodiments, a patient monitoring system includes one or more sensors configured to capture first data related to a patient and a monitoring device configured to receive the first data. In these and other embodiments, the patient monitoring system can include an image capture device configured to capture second data related to the patient. In these and still other embodiments, the one or more sensors can be configured to instruct the patient monitoring system to display the second data.

16 Claims, 5 Drawing Sheets

(51) Int. Cl.
*A61B 5/1455* (2006.01)
*G06T 7/00* (2017.01)

(56) References Cited

U.S. PATENT DOCUMENTS

| | | | |
|---|---|---|---|
| 5,800,360 A | 9/1998 | Kisner et al. | |
| 5,995,856 A | 11/1999 | Mannheimer et al. | |
| 6,668,071 B1 | 12/2003 | Minkin et al. | |
| 6,920,236 B2 | 7/2005 | Prokoski | |
| 7,431,700 B2 | 10/2008 | Aoki et al. | |
| 7,558,618 B1 | 7/2009 | Williams | |
| 8,149,273 B2 | 4/2012 | Liu | |
| 8,754,772 B2 | 6/2014 | Horng et al. | |
| 8,792,969 B2 | 7/2014 | Bernal et al. | |
| 8,971,985 B2 | 3/2015 | Bernal et al. | |
| 9,226,691 B2 | 1/2016 | Bernal et al. | |
| 9,282,725 B2 | 3/2016 | Jensen-Jarolim et al. | |
| 9,301,710 B2 | 4/2016 | Mestha et al. | |
| 9,402,601 B1 | 8/2016 | Berger et al. | |
| 9,436,984 B2 | 9/2016 | Xu et al. | |
| 9,443,289 B2 | 9/2016 | Xu et al. | |
| 9,504,426 B2 | 11/2016 | Kyal et al. | |
| 9,662,022 B2 | 5/2017 | Kyal et al. | |
| 9,693,693 B2 | 7/2017 | Farag et al. | |
| 9,693,710 B2 | 7/2017 | Mestha et al. | |
| 9,697,599 B2 | 7/2017 | Prasad et al. | |
| 9,750,461 B1 | 9/2017 | Telfort | |
| 9,839,756 B2 | 12/2017 | Klasek | |
| 9,943,371 B2 | 4/2018 | Bresch et al. | |
| 10,278,585 B2 | 5/2019 | Ferguson et al. | |
| 10,376,147 B2 | 8/2019 | Wood et al. | |
| 10,398,353 B2 | 9/2019 | Addison et al. | |
| 10,523,852 B2 | 12/2019 | Tzvieli et al. | |
| 10,588,779 B2 | 3/2020 | Vorhees et al. | |
| 10,667,723 B2 | 6/2020 | Jacquel et al. | |
| 10,702,188 B2 | 7/2020 | Addison et al. | |
| 10,874,331 B2 | 12/2020 | Kaiser et al. | |
| 10,939,824 B2 | 3/2021 | Addison et al. | |
| 10,939,834 B2 | 3/2021 | Khwaja et al. | |
| 2002/0137464 A1* | 9/2002 | Dolgonos | H04L 5/023 455/60 |
| 2004/0001633 A1 | 1/2004 | Caviedes | |
| 2004/0258285 A1 | 12/2004 | Hansen et al. | |
| 2005/0203348 A1 | 9/2005 | Shihadeh et al. | |
| 2007/0116328 A1 | 5/2007 | Sablak et al. | |
| 2008/0001735 A1 | 1/2008 | Tran | |
| 2008/0108880 A1* | 5/2008 | Young | G16H 40/67 600/300 |
| 2008/0279420 A1 | 11/2008 | Masticola et al. | |
| 2008/0295837 A1 | 12/2008 | McCormick et al. | |
| 2009/0304280 A1 | 12/2009 | Aharoni et al. | |
| 2010/0210924 A1 | 8/2010 | Parthasarathy et al. | |
| 2010/0236553 A1 | 9/2010 | Jafari et al. | |
| 2010/0249630 A1 | 9/2010 | Droitcour et al. | |
| 2010/0324437 A1 | 12/2010 | Freeman et al. | |
| 2011/0144517 A1 | 6/2011 | Cervantes | |
| 2011/0150274 A1 | 6/2011 | Patwardhan et al. | |
| 2012/0065533 A1 | 3/2012 | Carrillo et al. | |
| 2012/0075464 A1 | 3/2012 | Derenne et al. | |
| 2012/0243797 A1 | 9/2012 | Di Venuto Dayer et al. | |
| 2013/0267873 A1* | 10/2013 | Fuchs | A61B 5/743 600/595 |
| 2013/0271591 A1 | 10/2013 | Van Leest et al. | |
| 2013/0272393 A1 | 10/2013 | Kirenko et al. | |
| 2013/0275873 A1 | 10/2013 | Shaw et al. | |
| 2013/0324830 A1 | 12/2013 | Bernal et al. | |
| 2013/0324876 A1 | 12/2013 | Bernal et al. | |
| 2014/0023235 A1 | 1/2014 | Cennini et al. | |
| 2014/0052006 A1 | 2/2014 | Lee et al. | |
| 2014/0053840 A1 | 2/2014 | Liu | |
| 2014/0139405 A1 | 5/2014 | Ribble et al. | |
| 2014/0235976 A1 | 8/2014 | Bresch et al. | |
| 2014/0267718 A1 | 9/2014 | Govro et al. | |
| 2014/0272860 A1 | 9/2014 | Peterson et al. | |
| 2014/0275832 A1 | 9/2014 | Muehlsteff et al. | |
| 2014/0276104 A1 | 9/2014 | Tao et al. | |
| 2014/0330336 A1 | 11/2014 | Errico et al. | |
| 2014/0334697 A1 | 11/2014 | Kersten et al. | |
| 2014/0358017 A1 | 12/2014 | Op Den Buijs et al. | |
| 2014/0378810 A1 | 12/2014 | Davis et al. | |
| 2014/0379369 A1 | 12/2014 | Kokovidis et al. | |
| 2015/0003723 A1 | 1/2015 | Huang et al. | |
| 2015/0131880 A1 | 5/2015 | Wang et al. | |
| 2015/0157269 A1 | 6/2015 | Lisogurski et al. | |
| 2015/0223731 A1 | 8/2015 | Sahin | |
| 2015/0238150 A1 | 8/2015 | Subramaniam | |
| 2015/0265187 A1 | 9/2015 | Bernal et al. | |
| 2015/0282724 A1 | 10/2015 | McDuff et al. | |
| 2015/0301590 A1 | 10/2015 | Furst et al. | |
| 2015/0317814 A1 | 11/2015 | Johnston et al. | |
| 2016/0000335 A1 | 1/2016 | Khachaturian et al. | |
| 2016/0049094 A1 | 2/2016 | Gupta et al. | |
| 2016/0082222 A1 | 3/2016 | Garcia Molina et al. | |
| 2016/0140828 A1* | 5/2016 | DeForest | G08B 21/0211 340/539.12 |
| 2016/0143598 A1 | 5/2016 | Rusin et al. | |
| 2016/0151022 A1 | 6/2016 | Berlin et al. | |
| 2016/0156835 A1 | 6/2016 | Ogasawara et al. | |
| 2016/0174887 A1 | 6/2016 | Kirenko et al. | |
| 2016/0310084 A1 | 10/2016 | Banerjee et al. | |
| 2016/0317041 A1 | 11/2016 | Porges et al. | |
| 2016/0345931 A1 | 12/2016 | Xu et al. | |
| 2016/0367186 A1 | 12/2016 | Freeman et al. | |
| 2017/0007342 A1 | 1/2017 | Kasai et al. | |
| 2017/0007795 A1 | 1/2017 | Pedro et al. | |
| 2017/0055877 A1 | 3/2017 | Niemeyer | |
| 2017/0065484 A1 | 3/2017 | Addison et al. | |
| 2017/0071516 A1 | 3/2017 | Bhagat et al. | |
| 2017/0095215 A1 | 4/2017 | Watson et al. | |
| 2017/0095217 A1 | 4/2017 | Hubert et al. | |
| 2017/0119340 A1 | 5/2017 | Nakai et al. | |
| 2017/0147772 A1 | 5/2017 | Meehan et al. | |
| 2017/0164904 A1 | 6/2017 | Kirenko | |
| 2017/0172434 A1 | 6/2017 | Amelard et al. | |
| 2017/0173262 A1* | 6/2017 | Veltz | A61B 5/0022 |
| 2017/0238805 A1 | 8/2017 | Addison et al. | |
| 2017/0238842 A1* | 8/2017 | Jacquel | A61B 5/441 |
| 2017/0311887 A1 | 11/2017 | Leussler et al. | |
| 2017/0319114 A1 | 11/2017 | Kaestle | |
| 2018/0042486 A1 | 2/2018 | Yoshizawa et al. | |
| 2018/0042500 A1 | 2/2018 | Liao et al. | |
| 2018/0053392 A1 | 2/2018 | White et al. | |
| 2018/0104426 A1 | 4/2018 | Oldfield et al. | |
| 2018/0106897 A1 | 4/2018 | Shouldice et al. | |
| 2018/0169361 A1 | 6/2018 | Dennis et al. | |
| 2018/0217660 A1 | 8/2018 | Dayal et al. | |
| 2018/0228381 A1 | 8/2018 | Leboeuf et al. | |
| 2018/0310844 A1 | 11/2018 | Tezuka et al. | |
| 2018/0325420 A1 | 11/2018 | Gigi | |
| 2018/0333050 A1 | 11/2018 | Greiner et al. | |
| 2019/0050985 A1 | 2/2019 | Den Brinker et al. | |
| 2019/0142274 A1 | 5/2019 | Addison et al. | |
| 2019/0199970 A1 | 6/2019 | Greiner et al. | |
| 2019/0209046 A1 | 7/2019 | Addison et al. | |
| 2019/0209083 A1 | 7/2019 | Wu et al. | |
| 2019/0307365 A1 | 10/2019 | Addison et al. | |
| 2019/0311101 A1 | 10/2019 | Nienhouse | |
| 2019/0343480 A1 | 11/2019 | Shute et al. | |
| 2019/0380599 A1 | 12/2019 | Addison et al. | |
| 2019/0380807 A1 | 12/2019 | Addison et al. | |
| 2020/0046302 A1 | 2/2020 | Jacquel et al. | |
| 2020/0187827 A1 | 6/2020 | Addison et al. | |
| 2020/0202154 A1 | 6/2020 | Wang et al. | |
| 2020/0205734 A1 | 7/2020 | Mulligan et al. | |
| 2020/0237225 A1 | 7/2020 | Addison et al. | |
| 2020/0242790 A1 | 7/2020 | Addison et al. | |
| 2020/0250406 A1 | 8/2020 | Wang et al. | |
| 2020/0253560 A1 | 8/2020 | De Haan | |
| 2020/0289024 A1 | 9/2020 | Addison et al. | |
| 2020/0329976 A1 | 10/2020 | Chen et al. | |
| 2021/0068670 A1 | 3/2021 | Redtel | |
| 2021/0153746 A1 | 5/2021 | Addison et al. | |

(56) References Cited

U.S. PATENT DOCUMENTS

FOREIGN PATENT DOCUMENTS

| | | |
|---|---|---|
| CN | 112233813 A | 1/2021 |
| DE | 19741982 A1 | 10/1998 |
| EP | 2793189 B1 | 11/2016 |
| EP | 2428162 B1 | 8/2017 |
| EP | 3207862 A1 | 8/2017 |
| EP | 3207863 A1 | 8/2017 |
| EP | 3384827 A1 | 10/2018 |
| EP | 2772828 B1 | 1/2019 |
| JP | 2009544080 A | 12/2009 |
| JP | 2011130996 A | 7/2011 |
| KR | 101644843 B1 | 8/2016 |
| WO | 2004100067 A2 | 11/2004 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | 2019240991 A1 | 12/2019 |
| WO | 2020033613 A1 | 2/2020 |
| WO | 2021044240 A1 | 3/2021 |

OTHER PUBLICATIONS

Lawrence E, Navarro KF, Hoang D, Lim YY. Data collection, correlation and dissemination of medical sensor information in a WSN. In2009 Fifth International Conference on Networking and Services Apr. 20, 2009 (pp. 402-408). IEEE. (Year: 2009).*
Srinivas, Jangirala, Dheerendra Mishra, and Sourav Mukhopadhyay. "A mutual authentication framework for wireless medical sensor networks." Journal of medical systems 41.5 (2017): 80. (Year: 2017).*
Fischer, et al., "ReMoteCare: Health Monitoring with Streaming Video," ICMB '08, 7TH International Conference on Mobile Business, IEEE, Piscataway, NJ, Jul. 7, 2008, pp. 280-286 (MD40378PCT).
International Application No. PCT/US2021/015669 International Search Report and Written Opinion dated Apr. 21, 2021, 15 pages (MD40378PCT).
"European Search Report", European Patent Application No. 17156337. 2, Applicant: Covidien LP, dated Aug. 23, 2017, 10 pages.
"International Search Repod and Written Opinion", International Application No. PCT/US2018/060648, dated Jan. 28, 2019, 17 pages.
"International Search Repod and Written Opinion", International Application No. PCT/US2018/065492, dated Mar. 8, 2019, 12 pages.
"International Search Repod and Written Opinion", International Application No. PCT/US19/035433, dated Nov. 11, 2019, 17 pages.
"International Search Report and Written Opinion", International Application No. PCT/US2019/045600, dated Oct. 23, 2019, 19 pages.
"Invitation to Pay Additional Fees and Partial International Search Report", International Application No. PCT/US2019/035433, dated Sep. 13, 2019, 16 pages.
"Medical Electrical Equipment, Part 2-61: Particular requirements for basic safety and essential performance of pulse oximeter equipment", BSI Standards Publication, BS EN ISO 80601-2-61, 2011, 98 pages.
Aarts, Lonneke A.M., et al., "Non-contact heart rate monitoring utilizing camera photoplethysmography in neonatal intensive care unit—A Pilot Study", Early Human Development 89, 2013, pp. 943-948, 6 pages.

Abbas, A.K., et al., "Neonatal non-contact respiratory monitoring based on real-time infrared thermography", Biomed. Eng. Online, vol. 10, No. 93, 2011, 17 pages.
Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.
Addison, Paul S., et al., "Developing an algorithm for pulse oximetry derived respirator rate (RRoxi): a healthy volunteer study", J Clin comput, No. 26, 2012, pp. 45-51, 7 pages.
Addison, Paul S., et al., "Pulse oximetry-derived respiratory rate in general care floor patients", J. Clin Monit Comput, No. 29, 2015, pp. 113-120, 8 pages.
Addison, P.S., et al., "Video-based Heart Rate Monitoring across a Range of Skin Pigmentations during an Acute Hypoxic Challenge", J Clin Monit Comput, vol. 9, Nov. 9, 2017, 15 pages.
Amazon, "Dockem Koala Tablet Wall Mount Dock for iPad Air/ Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.
Amelard, et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.
Armanian, A. M., "Caffeine administration to prevent apnea in very premature infants", Pediatrics & Neonatology, 57 (5), 2016, pp. 408-412, 5 pages.
Barone, S, et al., "Computer-aided modelling of three-dimensional maxillofacial tissues through multi-modal Imaging", Proceedings of the Institution of Mechanical Engineers, Journal of Engineering in Medicine, Part H vol. 227, No. 2, Feb. 1, 2013, 1 page.
Barone, S, et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.
Bhattacharya, S., et al., "A Novel Classification Method for Predicting Acute Hypotensive Episodes in Critical Dare", 5th ACM Conference on Bioinformatics, Computational Bilogy and Health Informatics (ACM-BCB 2014), Newport Beach, USA, 2014, 10 pages.
Bhattacharya, S., et al., "Unsupervised learning using Gaussian Mixture Copula models", 21st International Conference on Computational Statistics (COMPSTAT 2014), Geneva, Switzerland, 2014, pp. 523-530, 8 pages.
Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.
Bousefsaf, Frederic, et al., "Continuous wavelet filtering on webcam photoplethysmographic signals to remotely assess the instantaneous heart rate", Biomedical Signal Processing and Control 8, 2013, pp. 568-574, 7 pages.
Bruser, C., et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.
Cennini, Giovanni, et al., "Heart rate monitoring via remote photoplethysmography with motion artifacts reduction", Optics Express, vol. 18, No. 5, Mar. 1, 2010, pp. 4867-4875, 9 pages.
Colantonio, S., et al., "A smart mirror to promote a healthy lifestyle", Biosystems Engineering. vol. 138, Innovations in Medicine and Healthcare, Oct. 2015, pp. 33-43, 11 pages.
Cooley, et al., "An Alorithm for the Machine Calculation of Complex Fourier Series", Aug. 17, 1964, pp. 297-301, 5 pages.
Di Fiore, J.M., et al., "Intermittent hypoxemia and oxidative stress in preterm infants", Respiratory Physiology & Neurobiology, No. 266, 2019, pp. 121-129, 25 pages.
Fei, J., et al., "Thermistor at a distance: unobtrusive measurement of breathing", IEEE Transactions on Biomedical Engineering, vol. 57, No. 4, 2010, pp. 968-998, 11 pages.
Feng, Litong, et al., "Dynamic ROI based on K-means for remote photoplethysmography", IEE International Conference on Accoustics, Speech and Signal Processing (ICASSP), Apr. 2015, pp. 1310-1314, 5 pages.

(56) References Cited

OTHER PUBLICATIONS

George, et al., "Respiratory Rate Measurement From PPG Signal Using Smart Fusion Technique", International Conference on Engineering Trends and Science & Humanities (ICETSH-2015), 2015, 5 pages.

Goldman, L.J., "Nasal airflow and thoracoabdominal motion in children using infrared thermographic video processing". Pediatric Pulmonology, vol. 47, No. 5, 2012, pp. 476-486, 11 pages.

Grimm, T., et al., "Sleep position classification from a depth camera using bed aligned maps", 23rd International Conference on Pattern Recognition (ICPR), Dec. 2016, pp. 319-324, 6 pages.

Gsmarena, "Apple iPad Pro 11 (2018)", https://www.gsmarena.com/apple_ipad_pro_11_(2018)-9386.pjp, viewed on Nov. 16, 2021, 1 page.

Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.

Han, J., et al., "Visible and infrared image registration in man-made environments employing hybrid visuals features", Pattern Recognition Letters, vol. 34, No. 1, 2013, pp. 42-51, 10 pages.

Huddar, V., et al., "Predicting Postoperative Acute Respiratory Failure in Critical Care using Nursing Notes and Physiological Signals", 36th Annual International Conference of IEEE Engineering in Medicine and Biology Society (IEEE EMBC 2014), Chicago, USA, 2014, pp. 2702-2705, 4 pages.

Hyvarinen, A., et al., "Independent Component Analysis: Algorithms and Applications", Neural Networks, vol. 13, No. 4, 2000, pp. 411-430, 31 pages.

Javadi, M., et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.

Jopling, M. W., et al., "Issues in the Laboratory Evaluation of Pulse Oximeter Performance", Anesth. Analg., No. 94, 2002, pp. S62-S68, 7 pages.

Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.

Klaessens, J.H.G.M., et al., "Non-invasive skin oxygenation imaging using a multi-spectral camera system: Effectiveness of various concentration algorithms applied on human skin", Proc. of SPIE, vol. 7174 717408-1, 2009, 14 pages.

Kong, Lingqin, et al., "Non-contact detection of oxygen saturation based on visible light imaging device using ambient light", Optics Express, vol. 21, No. 15, Jul. 29, 2013, pp. 17646-17471, 8 pages.

Kortelainen, J.M., et al., "Sleep staging based on signals acquired through bed sensor", IEEE Transactions on Informational Technology in Biomedicine, vol. 14, No. 3, May 2010, pp. 776-785, 10 pages.

Kumar, M., et al., "Distance PPG: Robust non-contact vital signs monitoring using a camera", Biomedical Optics Express, vol. 6, No. 5, May 1, 2015, 24 pages.

Kwon, Sungjun, et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177, 4 pages.

Lai, C.J., et al., "Heated humidified high-flow nasal oxygen prevents intraoperative body temperature decrease in non-intubated thoracoscopy", Journal of Anesthesia, Oct. 15, 2018, 8 pages.

Li, et al., "A Non-Contact Vision-Based System for Respiratory Rate Estimation", IEEE 978-1-4244-7929-0/14, 2014, pp. 2119-2122, 4 pages.

Liu, H., et al., "A Novel Method Based on Two Cameras for Accurate Estimation of Arterial Oxygen Saturation", BioMedical Engineering Online, vol. 14, No. 52, 2015, 18 pages.

Liu, S., et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Liu, C., et al., "Motion Magnification", ACM Transactions on Graphics (TOG), vol. 24, No. 3, 2005, pp. 519-526, 8 pages.

Lv, et al., "Class Energy Image Analysis for Video Sensor-Based Gait Recognition: A Review", Sensors, No. 15, 2015, pp. 932-964, 33 pages.

McDuff, Daniel J., et al., "A Survey of Remote Optical Photoplethysmographic Imaging Methods", IEEE 987-1-4244-0270-1/15, 2015, pp. 6398-6404, 7 pages.

Mestha, L.K., et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.

Nguyen, et al., "3D shape, deformation and vibration measurements using infrared Kinect sensors and digital image correlation", Applied Optics, vol. 56, No. 32, Nov. 10, 2017, 8 pages.

Ni, et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.

Nisar, et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.

Pereira, C., et al., "Noncontact Monitoring of Respiratory Rate in Newborn Infants Using Thermal Imaging", IEEE Transactions on Biomedical Engineering, Aug. 23, 2018, 10 pages.

Poh, et al., "Advancements in Noncontact, Multiparameter Physiological Measurements Using a Webcam", IEEE Transactions on Biomedical Engineering, vol. 58, No. 1, Jan. 2011, pp. 7-11, 5 pages.

Poh, et al., "Non-contact, automated cardiac pulse measurements using video imaging and blind source separation", OPT Express 18, 2010, pp. 10762-10774, 14 pages.

Povsic, Klemen, et al., "Real-Time 3D visualization of the thoracoabdominal surface during breathing with body movement and deformation extraction", Physiological Measurement, vol. 36, No. 7, May 28, 2015, pp. 1497-1516, 22 pages.

Prochazka, et al., "Microsoft Kinect Visual and Depth Sensors for Breathing and Heart Rate Analysis", Senors, vol. 16, No. 7, Jun. 28, 2016, 11 pages.

Rajan, V., et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.

Rajan, V., et al., "Dependency Clustering of Mixed Data with Gaussian Mixture Copulas", 25th International Joint Conference on Artificial Intelligence IJCAI, New York, USA, 2016, pp. 1967-1973, 7 pages.

Reisner, A., et al., "Utility of the Photoplethysmogram in Circulatory Monitoring", American Society of Anesthesiologist, May 2008, pp. 950-958, 9 pages.

Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622, 12 pages.

Rubinstein, M, "Analysis and Visualization of Temporal Variations in Video", Department of Electrical Engineering and Computer Science, Massachusetts Institute of Technology, Feb. 2014, 118 pages.

Scalise, Lorenzo, et al., "Heart rate measurement in neonatal patients using a webcamera", Department of Industrial Engineering and Mathematical Science, Italy, 978-1-4673-0882-3/12, EEE, 2012, 4 pages.

Schaerer, J., et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.

Sengupta, A., et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.

(56) References Cited

OTHER PUBLICATIONS

Shah, Nitin, et al., "Performance of three new-generation pulse oximeters during motion and low perfursion in volunteers". Journal of Clinical Anesthesia, No. 24, 2012, pp. 385-391, 7 pages.

Shao, Dangdang, et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.

Shrivastava, H., et al., "Classification with Imbalance: A Similarity-based Method for Predicting Respiratory Failure", IEEE International Conference on Bioinformatics and Biomedicine (IEEE BIBM2015), Washington, DC, USA, 2015, pp. 707-714, 8 pages.

Sun, Yu, et al., "Motion-compensated noncontact imaging photoplethysmography to monitor cardiorespiratory status during exercise", Journal of Biomedical Optics, vol. 16, No. 7, Jul. 1, 2011, 10 pages.

Sun, Yu, et al., "Noncontact imaging photoplethysmography to effectively access pulse rate variability", Journal of Biomedical Optics, vol. 18(6), Jun. 2013, 10 pages.

Tamura, et al., "Wearable Photoplethysmographic Sensors—Past & Present", Electronics, vol. 3, 2014, pp. 282-302, 21 pages.

Tarassenko, L., et al., "Non-contact video-based vital sign monitoring using ambient light and auto-regressive models", Institute of Physics and Engineering in Medicine, vol. 35, 2014, pp. 807-831, 26 pages.

Teichmann, D., et al., "Non-Contact monitoring techniques—Principles and applications", In Proc. of IEEE International Conference of the Engineering in Medicine and Biology Society (EMBC), San Diego, CA, 2012, pp. 1302-1305, 4 pages.

Verkruysee, Wim, et al., "Calibration of Contactless Pulse Oximetry", Anesthesia & Analgesia, vol. 124, No. 1, Jan. 2017, pp. 136-145, 10 pages.

Villarroel, Mauricio, et al., "Continuous non-contact vital sign monitoring in neonatal intensive care unit", Healthcare Technology Letters, vol. 1, Issue 3, 2014, pp. 87-91, 5 pages.

Wadhwa, N., et al., "Phase-Based Video Motion Processing", MIT Computer Science and Ailincial Intelligence Lab, Jul. 2013, 9 pages.

Wadhwa, N., et al., "Riesz pyramids for fast phase-based video magnification", In Proc. of IEEE International Conference on Computational Photography (ICCP), Santa Clara, CA, 2014, 10 pages.

Wang, W., et al., "Exploiting spatial redundancy of image sensor for motion robust rPPG", IEEE Transactions on Biomedical Engineering, vol. 62, No. 2, 2015, pp. 415-425, 11 pages.

Wu, H.Y., et al., "Eulerian video magnification for revealing subtle changes in the world", ACM Transactions on Graphics (TOG), vol. 31, No. 4, 2012, pp. 651-658, 8 pages.

Wulbrand, H., et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.

Zaunseder, et al., "Spatio-temporal analysis of blood perfusion by imaging photoplethysmography", Progress in Biomedical Optics and Imaging, SPIE—International Society for Optical Engineering, vol. 10501, Feb. 20, 2018, 15 pages.

Zhou, J., et al., "Maximum parsimony analysis of gene copy number changes in tumor phylogenetics", 15th International Workshop on Algorithms in Bioinformatics WABI 2015, Atlanta, USA, 2015, pp. 108-120, 13 pages.

* cited by examiner

ATTACHED SENSOR ACTIVATION OF ADDITIONALLY-STREAMED PHYSIOLOGICAL PARAMETERS FROM NON-CONTACT MONITORING SYSTEMS AND ASSOCIATED DEVICES, SYSTEMS, AND METHODS

FIELD

The present technology is generally related to non-contact monitoring systems for patients, used in conjunction with attached patient sensors.

BACKGROUND

Many conventional medical monitors require attachment of a sensor to a patient in order to detect physiologic signals from the patient and to transmit detected signals through a cable to the monitor. These monitors process the received signals and determine vital signs such as the patient's pulse rate, respiration rate, and arterial oxygen saturation. For example, a pulse oximeter is a finger sensor that can include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a field of patient monitoring that uses one or more remote video cameras to detect physical attributes of the patient. This type of monitoring can also be called "non-contact" monitoring in reference to the remote video sensor(s), which does/do not contact the patient. The remainder of this disclosure offers solutions and improvements in this field.

SUMMARY

The techniques of this disclosure generally relate to a patient monitoring system including a non-contact monitoring component, used in conjunction with one or more attached patient sensors, with the sensor(s) activating additionally streamed physiological parameters from the non-contact monitoring system.

In one aspect, a first sensor in contact with a patient provides first data to determine one or more patient parameters. A non-contact video monitoring system including an image capture device is programmed to capture second data related to the patient. A monitoring device is configured to receive and display said first data; and either said first sensor or an associated first sensor device is configured to provide instructions to the monitoring device to display said second data.

In another aspect, an additional connecting element is associated with the first sensor, the additional connecting element configured to receive the first data from the one or more sensors and to transmit the first data to the monitoring device.

In another aspect, the first sensor or associated first sensor device is configured to provide instruction as an encrypted key.

In another aspect, the non-contact video monitoring system is programmed to define one or more regions of interest (ROI's) on a patient, capture the second data related to the patient, wherein the second data includes two or more images of the ROI's, and to measure changes in depths of the ROI's across the two or more images of the ROI's.

In another aspect, the image capture device includes a depth sensing camera, an RGB camera, and/or an infrared camera.

In another aspect, instructions to the monitoring device are configured to: allow the monitoring device to include the second data directly onto a current display screen; allow the monitoring device to reconfigure a current screen to display the second data; and/or allow for separate pages to be accessible on the monitoring device for display of the second data.

In other aspects, the first and second data are combined at a monitoring device or are combined prior to receipt at a monitoring device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

Figure 1:
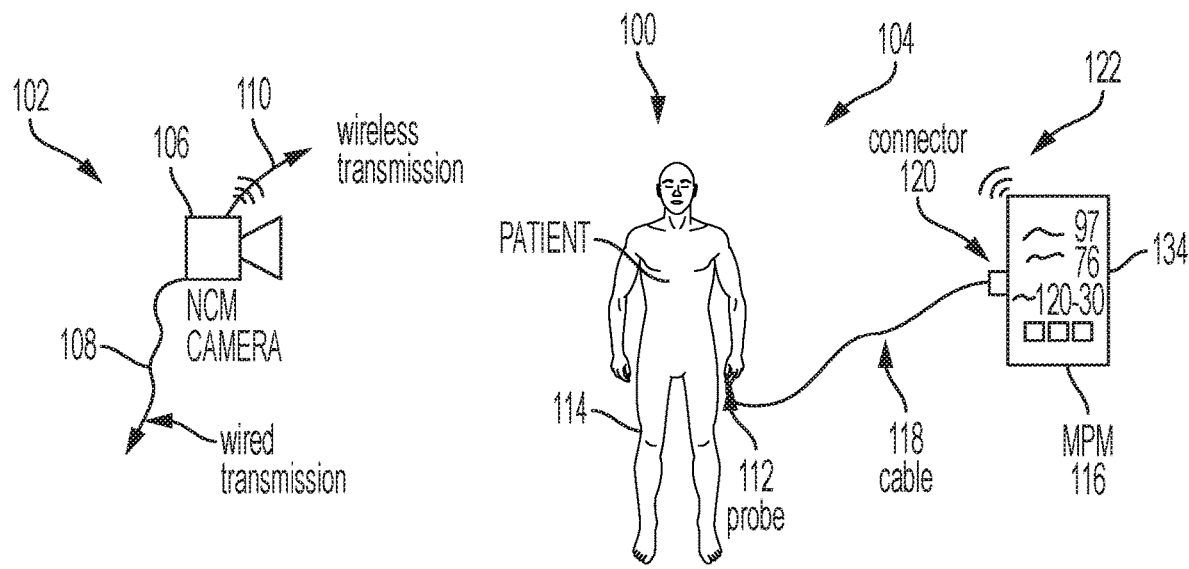
FIG. 1 is a schematic view of a patient monitoring system configured with both attached and non-contact monitoring components, in accordance with various embodiments of the present technology.

The following disclosure describes patient monitoring devices, systems, and associated methods for detecting and/or monitoring one or more patient parameters, such as tidal volume, respiratory rate, minute volume, patient movement, temperature, blood pressure, heart rate, arterial oxygen saturation, and/or others. As described in greater detail below, devices, systems, and/or methods configured in accordance with embodiments of the present technology are configured to capture one or more images (e.g., a video sequence) of a patient or a portion of a patient (e.g., a patient's torso) within a field of view of a non-contact detector (e.g., an image capture device). The devices, systems, and/or methods can measure changes in depths of regions (e.g., one or more pixels or groups of pixels) in the captured images over time. Based, at least in part, on these measurements, the devices, systems, and/or methods can determine various respiratory parameters of a patient, including tidal volume, minute volume, and respiratory rate, among others. In these and other embodiments, the device, systems, and/or methods can analyze the respiratory parameters and can trigger alerts and/or alarms when the devices, systems, and/or methods detect one or more breathing abnormalities.

Additionally, devices, systems, and/or methods configured in accordance with embodiments of the present technology can include one or more sensors or probes associated with (e.g., contacting) a patient that can be configured to capture data (e.g., temperature, blood pressure, heart rate, arterial oxygen saturation, etc.) related to a patient. The devices, systems, and/or methods can transmit the captured data to a monitoring device, hub, mobile patient management system (MPM), or the like. In some embodiments, the devices, systems, and/or methods can analyze the captured data to determine and/or monitor one or more patient parameters. In these and other embodiments, the devices, systems, and/or methods can use the data captured by the one or more sensors or probes in conjunction with data captured using a non-contact detector. In these and still other embodiments, the devices, systems, and/or methods can trigger alerts and/or alarms when the devices, systems, and/or methods detect one or more patient parameter abnormalities.

In some embodiments, one or more sensors or probes associated with (e.g., contacting) a patient can be configured to capture data related to a patient and can be configured to activate additionally streamed physiological parameters from non-contact monitoring (NCM) devices. In such cases, one or more sensors or probes and/or one or more associated intermediary devices (e.g., an additional connecting element (ACE)) can be configured to communicate with and instruct a monitoring device, such as a hub, mobile patient management system (MPM), or the like (note that a monitoring device could also be a clinician's data tablet, a central data collection and display system, etc.), to start receiving physiological data from an NCM camera and/or allow such data to be displayed on the screen.

In exemplary embodiments such instruction by a sensor, probe or associated device comprises a key that is transmitted to (either via a wired or wireless connection) and read by the monitoring device. The key can be configured to: allow the monitoring device to include the additional physiological information directly onto a current display screen; allow the device or system to reconfigure a current screen to display the additional physiological information; and/or allow for separate pages to be accessible on the device or system for display of the additional physiological information.

In some exemplary embodiments, sensors or probes that are configured to provide such instruction are provided with marking, for example different color coding, packaging, labeling, etc., to distinguish from standard sensors or probes. In some embodiments, such sensors or probes are configured with a unique or different connector shape and/or connector pin configuration relative to standard sensors or probes.

In some exemplary embodiments, a wireless receiver or additional connecting element (ACE) can collect or pass through the patient sensor or probe information (e.g., pulse oximeter information, or a combination of different types of information from plural patient sensors or probes) as well as receive the additional (NCM) physiological information, passing all of this information on to a monitoring device. Additionally, different wireless receivers or ACE components may be configured to switch on different physiological parameters, for example with one configured only to include respiratory parameters (e.g., respiratory rate, tidal volume, minute volume and central and obstructive apnea detection), whereas others could be configured to only include patient activity and posture information, etc. Accordingly, one or more ACE components may be configured to simultaneously provide information to a monitoring device.

In some embodiments, one or more ACE components may be configured only to when an appropriate/compatible probe is attached. Additionally, it should be recognized that various additional types of sensors and probes are contemplated, including without limitation regional saturation probes, depth of anesthesia (EEG) probes, capnography sidestream probes, etc. Further, the present disclosure contemplates other sources of additional physiological information (in addition to or instead of NCM), including temperature, $ETCO_2$, $rSO_2$ monitors, etc. Also as has been noted above, in some embodiments, a wireless (for example, electromagnetic, LiFi, sonar, etc.) system can be used for one or more transmission paths.

In some exemplary embodiments, data streams are combined and/or switched on prior to sending the streams to the monitoring device.

Specific details of several embodiments of the present technology are described herein with reference to FIGS. 1-6. Although many of the embodiments are described with respect to devices, systems, and methods for detection and/or monitoring of one or more parameters of a human patient, other applications and other embodiments in addition to those described herein are within the scope of the present technology. For example, at least some embodiments of the present technology can be useful for detection and/or monitoring of one or more parameters of other animals and/or in non-patients (e.g., elderly or neonatal individuals within their homes, individuals in a search and rescue or stranded context, etc.). It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

Figure 2:
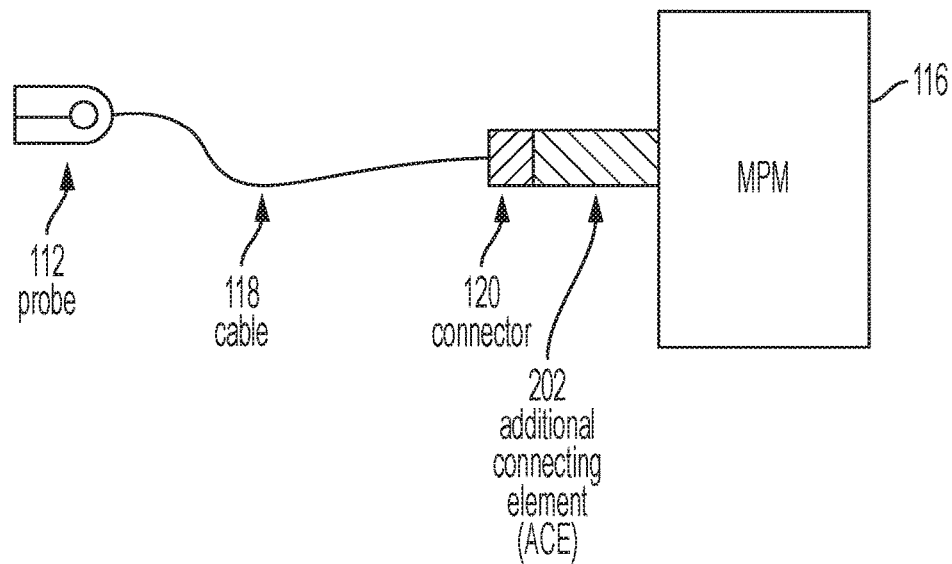
FIG. 2 is a schematic view of a patient monitoring system having a probe with an additional connecting element, configured in accordance with various embodiments of the present technology.

FIG. 1 is a schematic view of an exemplary monitoring system, shown generally at 100, including a non-contact monitoring (NCM) system, shown generally at 102 and a patient attached probe system, shown generally at 104. An exemplary NCM camera 106 is illustrated in an out-of-contact position with optional wired 108 and wireless 110 transmission paths. The patient attached probe system 104 shows an exemplary finger probe 112, attached to a patient 114, and an exemplary mobile patient monitoring (MPM) device 116, connected to the probe/sensor 112 via a cable 118 and a connector 120. An optional wireless pathway to/from the device is shown generally at 122. FIG. 2 is a schematic view of an exemplary connected probe 112 and MPM 116, with the cable 118 and connector 120 first connecting to an additional connecting element (ACE) 202.

In some embodiments, the monitoring device can be a monitor with a screen 134 (e.g., to display various information, such as a power on/off button, one or more patient parameters, one or more alerts and/or alarms, etc.). The monitoring device can be attached to, be worn, and/or otherwise be carried by a patient 114. For example, the monitoring device can be attached to and/or worn by the patient 114 at the patient's upper arm, at the patient's belt, on the patient's wrist (e.g., as a watch and/or using a band), etc. In some embodiments, the monitoring device can be sewn into the patient's clothing. In these and other embodiments, the monitoring device can be a mobile device, such as a mobile phone, tablet, or laptop.

In the embodiments illustrated in FIGS. 1 and 2, one or more probes/sensors 112 include a pulse oximeter attached to a finger of the patient. In these and other embodiments, the one or more sensors 112 can include other sensors in addition to or in lieu of the pulse oximeter, such as electrodes, temperature sensors, blood pressure cuffs, etc. The one or more sensors 112 can be used to perform various tests and/or to capture various information and data relating to the patient 114. For example, the one or more sensors 112 can be used to capture an electrocardiogram (ECG) signal and/or an electroencephalogram (EEG) signal of the patient. In these and other embodiments, the one or more sensors 112 can capture the patient's arterial oxygen saturation, temperature, blood pressure, and/or other patient parameters (e.g., systolic and diastolic pressure, heart rate, respiratory rate, average temperature, etc.).

Information captured by the one or more sensors 112 can be stored and/or processed by the one or more sensors 112 and/or by the monitoring device. For example, the one or more sensors 112 can store captured information and/or can locally process the captured information (e.g., to determine one or more patient parameters). In these and other embodiments, the one or more sensors 112 can transmit the raw, captured information and/or the locally processed data to the monitoring device. For example, the one or more sensors 112 can include a wireless transmitter (not shown) to transfer the data directly to the monitoring device via a wired or wireless connection (not shown). In turn, the monitoring device can store and/or process the information received from the one or more sensors 112 (e.g., to determine one or more patient parameters). In these and other embodiments, the monitoring device can transfer the raw, captured information and/or processed data to a central unit (not shown), such as a central hospital station, via a wired or wireless connection (not shown).

Additionally or alternatively, the one or more sensors 112 can transmit the captured information and/or the locally processed data to a relay (not shown) (e.g., a band attached to the patient) via one or more wired and/or wireless connections. In some embodiments, a relay can store and/or process data received from the one or more sensors. In these and other embodiments, the relay can include a wireless transmitter that can be used to transmit the captured information and/or the processed data to the monitoring device via a wireless connection.

Figure 3:
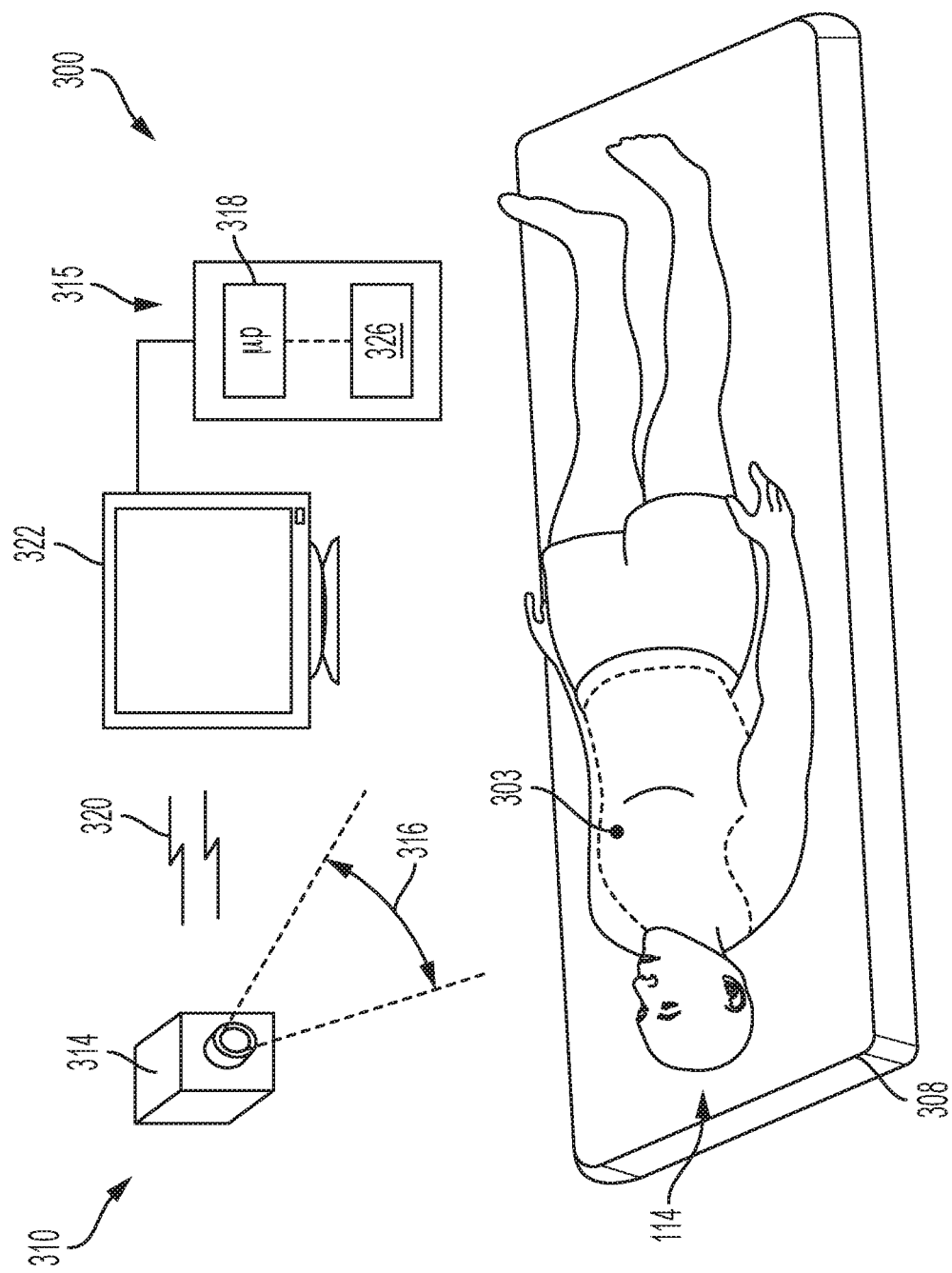
FIG. 3 is a schematic view of patient monitoring systems configured in accordance with various embodiments of the present technology.

FIG. 3 is a schematic view of a patient 114 and a video-based patient monitoring system 300 configured in accordance with various embodiments of the present technology. The system 300 includes a non-contact detector 310 and a computing device 315. In some embodiments, the detector 310 can include one or more image capture devices 314, such as one or more video cameras. The non-contact detector 310 of the system 300 is placed remote from the patient 114. More specifically, the image capture device 314 of the non-contact detector 310 is positioned remote from the patient 114 in that it is spaced apart from and does not contact the patient 114. The image capture device 314 includes a detector exposed to a field of view (FOV) 316 that encompasses at least a portion of the patient 114.

The image capture device 314 can capture a sequence of images over time. The image capture device 314 can be a depth sensing camera, such as a Kinect camera from Microsoft Corp. (Redmond, Wash.). A depth sensing camera can detect a distance between the camera and objects within its field of view. Such information can be used, as disclosed herein, to determine that a patient 114 is within the FOV 316 of the image capture device 314 and/or to determine one or more ROI's to monitor on the patient 114. Once an ROI is identified, the ROI can be monitored over time, and the changes in depths of regions (e.g., pixels) within the ROI can represent movements of the patient 114 (e.g., associated with breathing). As described in greater detail in U.S. patent application Ser. No. 16/219,360, U.S. Provisional Patent Application Ser. No. 62/779,964 and U.S. Provisional Patent Application Ser. No. 62/797,519, those movements, or changes of regions within the ROI, can be used to determine various patient parameters, such as various breathing parameters, including tidal volume, minute volume, respiratory rate, etc. Those movements, or changes of regions within the ROI, can also be used to detect various patient parameter abnormalities, as discussed in greater detail in U.S. Provisional Patent Application Ser. Nos. 62/716,724 and 62/779,964. The various patient parameter abnormalities can include, for example, apnea, rapid breathing (tachypnea), slow breathing, intermittent or irregular breathing, shallow breathing, obstructed and/or impaired breathing, and others. The entire disclosures of U.S. patent application Ser. No. 16/219,360 and U.S. Provisional Patent Application Ser. Nos. 62/716,724, 62/779,964 and 62/797,519 are incorporated herein by reference.

In these and other embodiments, the image capture device can be an RGB (red green blue) camera or an infrared camera. An RGB camera can detect slight color changes within its field of view. Such information can be used, as disclosed herein, to determine that a patient 114 is within the FOV 316 of the image capture device 314 and/or to determine one or more ROI's to monitor on the patient 114. Once an ROI is identified, the ROI can be monitored over time, and the changes in color of regions (e.g., pixels) within the ROI can represent various information related to the patient 114. As described in greater detail in U.S. patent application Ser. No. 16/188,969 those color changes can be used to detect optical signals associated with one or more medical devices, such as a pulse oximeter attached to the patient. Those color changes can also be used to determine and/or monitor various vital signs of the patient, including pulse rate, respiration rate, and arterial oxygen saturation, as discussed in greater detail in U.S. patent application Ser. Nos. 15/432,057, 15/432,063 and 62/797,519. Additionally, or alternatively, as discussed in greater detail in U.S. Provisional Patent Application Ser. Nos. 62/685,485 and 62/695,244, those color changes can also be used in a surgical setting to monitor and/or assess blood flow in the ROI by detecting occlusions and/or monitoring pulsation, pulsation strength, and/or perfusion. The entire disclosures of U.S. patent application Ser. Nos. 16/188,969, 15/432,057, and 15/432,063 and U.S. Provisional Patent Application Ser. Nos. 62/685,485 and 62/695,244 are incorporated herein by reference.

In some embodiments, the system 300 can receive user input to identify a starting point for defining a ROI. For example, an image can be reproduced on a display 322 of the system 300 (or on the display of the monitoring device 116), allowing a user of the system 300 to select a patient 114 for monitoring (which can be helpful where multiple objects are within the FOV 316 of the image capture device 314) and/or allowing the user to select a point on the patient 114 from which a ROI can be determined (such as the point 303 on the chest of the patient 114). In other embodiments, other methods for identifying a patient 114, for identifying points on the patient 114, and/or for defining one or more ROI's can be used. For example, a user can select a patient 114 for monitoring and a point on a patient bed 308 (which can be helpful in defining one or more ranges of depths to be used in measurements taken by a non-contact detector).

Figure 4:
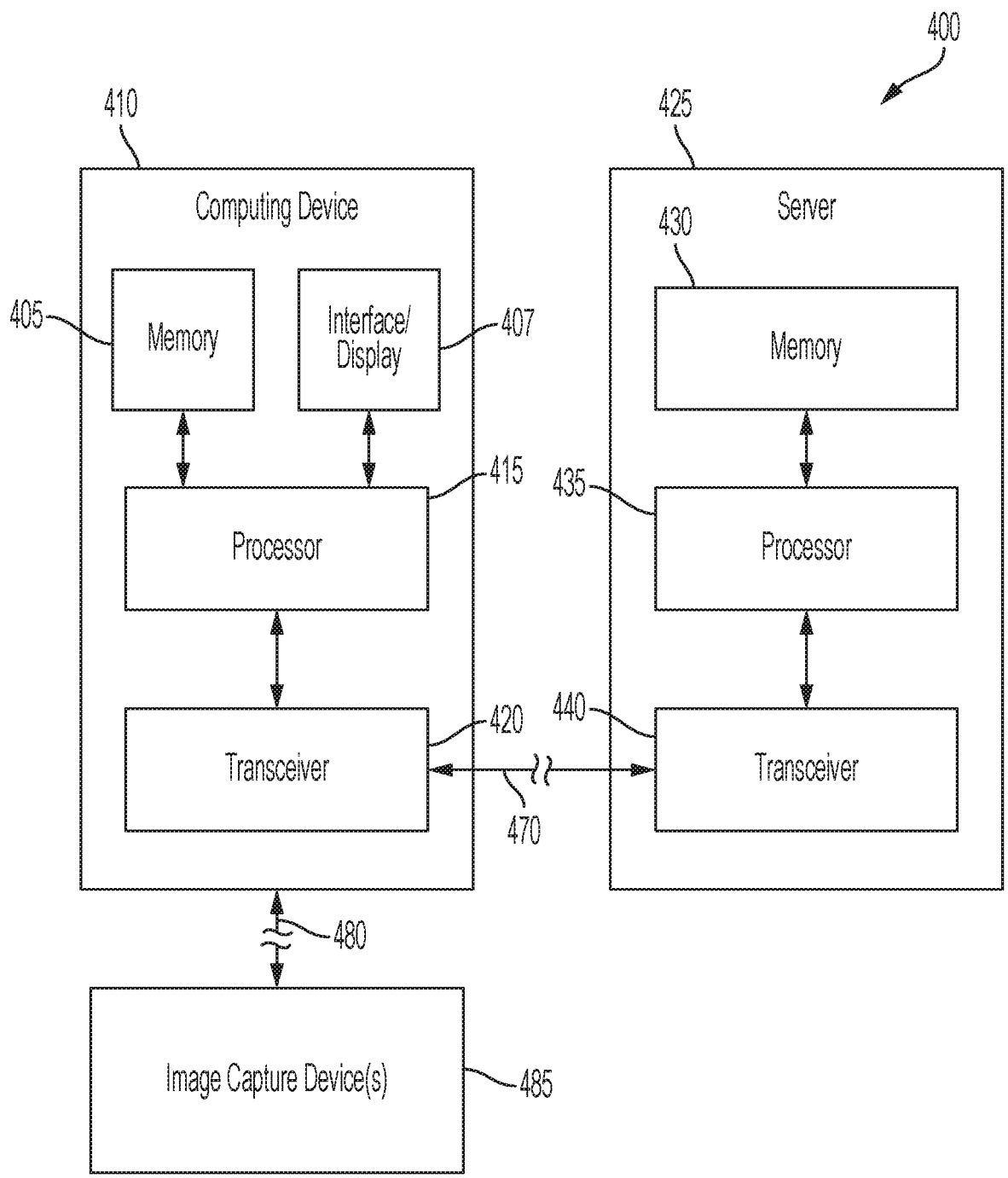
FIG. 4 is a block diagram illustrating a patient monitoring system having a computing device, a server, and one or more image capture devices, and configured in accordance with various embodiments of the present technology.

The images detected by the image capture device 314 can be sent to the computing device 315 through a wired or wireless connection 320. The computing device 315 can include a processor 318 (e.g., a microprocessor), the display 322, and/or hardware memory 326 for storing software and computer instructions. Sequential image frames of the patient 114 are recorded by the image capture device 314 and sent to the processor 318 for analysis. The display 322 can be remote from the image capture device 314, such as a video screen positioned separately from the processor 318 and the memory 326. Other embodiments of the computing device 315 can have different, fewer, or additional components than shown in FIG. 3. In some embodiments, the computing device 315 can be a server. In other embodiments, the computing device 315 of FIG. 3 can be additionally connected to a server (e.g., as shown in FIG. 4 and discussed in greater detail below). The captured images/video can be processed or analyzed at the computing device 315 and/or a server to determine a variety of parameters (e.g., tidal volume, minute volume, respiratory rate, etc.) of a patient.

FIG. 4 is a block diagram illustrating a patient monitoring system 400 (e.g., the patient monitoring system 100 shown in FIG. 1 and the video-based patient monitoring system 300 shown in FIG. 3, having a computing device 410, a server 425, and one or more image capture devices 485, and configured in accordance with various embodiments of the present technology. In various embodiments, fewer, additional, and/or different components can be used in the system 400. The computing device 410 includes a processor 415 that is coupled to a memory 405. The processor 415 can store and recall data and applications in the memory 405, including applications that process information and send commands/signals according to any of the methods disclosed herein. The processor 415 can also (i) display objects, applications, data, etc. on an interface/display 407 and/or (ii) receive inputs through the interface/display 407. As shown, the processor 415 is also coupled to a transceiver 420.

The computing device 410 can communicate with other devices, such as the server 425 and/or the image capture device(s) 485 via (e.g., wired or wireless) connections 470 and/or 480, respectively. For example, the computing device 410 can send to the server 425 information determined about a patient from images and/or other data captured by the image capture device(s) 485 and/or one or more other sensors or probes. The computing device 410 can be located remotely from the image capture device(s) 485, or it can be local and close to the image capture device(s) 485 (e.g., in the same room). In various embodiments disclosed herein, the processor 415 of the computing device 410 can perform the steps disclosed herein. In other embodiments, the steps can be performed on a processor 435 of the server 425. In some embodiments, the various steps and methods disclosed herein can be performed by both of the processors 415 and 435. In some embodiments, certain steps can be performed by the processor 415 while others are performed by the processor 435. In some embodiments, information determined by the processor 415 can be sent to the server 425 for storage and/or further processing.

In some embodiments, the image capture device(s) 485 are remote sensing device(s), such as depth sensing video camera(s) In some embodiments, the image capture device(s) 485 can be or include some other type(s) of device(s), such as proximity sensors or proximity sensor arrays, heat or infrared sensors/cameras, sound/acoustic or radio wave emitters/detectors, or other devices that include a field of view and can be used to monitor the location and/or characteristics of a patient or a region of interest (ROI) on the patient. Body imaging technology can also be utilized according to the methods disclosed herein. For example, backscatter x-ray or millimeter wave scanning technology can be utilized to scan a patient, which can be used to define and/or monitor a ROI. Advantageously, such technologies can be able to "see" through clothing, bedding, or other materials while giving an accurate representation of the patient's skin facet. This can allow for more accurate measurements, particularly if the patient is wearing baggy clothing or is under bedding. The image capture device(s) 485 can be described as local because they are relatively close in proximity to a patient such that at least a part of a patient is within the field of view of the image capture device(s) 485. In some embodiments, the image capture device(s) 485 can be adjustable to ensure that the patient is captured in the field of view. For example, the image capture device(s) 485 can be physically movable, can have a changeable orientation (such as by rotating or panning), and/or can be capable of changing a focus, zoom, or other characteristic to allow the image capture device(s) 485 to adequately capture images of a patient and/or a ROI of the patient. In various embodiments, for example, the image capture device(s) 485 can focus on a ROI, zoom in on the ROI, center the ROI within a field of view by moving the image capture device(s) 485, or otherwise adjust the field of view to allow for better and/or more accurate tracking/measurement of the ROI.

The server 425 includes a processor 435 that is coupled to a memory 430. The processor 435 can store and recall data and applications in the memory 430. The processor 435 is also coupled to a transceiver 440. In some embodiments, the processor 435, and subsequently the server 425, can communicate with other devices, such as the computing device 410 through the connection 470.

The devices shown in the illustrative embodiment can be utilized in various ways. For example, either the connections 470 and 480 can be varied. Either of the connections 470 and 480 can be a hard-wired connection. A hard-wired connection can involve connecting the devices through a USB (universal serial bus) port, serial port, parallel port, or other type of wired connection that can facilitate the transfer of data and information between a processor of a device and a second processor of a second device. In another embodiment, either of the connections 470 and 480 can be a dock where one device can plug into another device. In other embodiments, either of the connections 470 and 480 can be a wireless connection. These connections can take the form of any sort of wireless connection, including, but not limited to, Bluetooth connectivity, Wi-Fi connectivity, infrared, visible light, radio frequency (RF) signals, or other wireless protocols/methods. Other possible modes of wireless communication can include near-field communications, such as passive radio-frequency identification (RFID) and active RFID technologies. RFID and similar near-field communications can allow the various devices to communicate in short range when they are placed proximate to one another. In some embodiments, two or more devices in the patient monitoring system 400 can together create a dynamic mesh network that includes connections 470 and/or 480. In these and other embodiments, data captured by and/or received at one device of the system 400 may be sent to and/or through other devices of the system 400 (e.g., to reach the server(s)), hence improving wireless coverage. In these and still other embodiments, the various devices can connect through an internet (or other network) connection. That is, either of the connections 470 and 480 can represent several different computing devices and network components that allow the various devices to communicate through the internet, either through a hard-wired or wireless connection. Either of the connections 470 and 480 can also be a combination of several modes of connection.

The configuration of the devices in FIG. 4 is merely one physical system 400 on which the disclosed embodiments can be executed. Other configurations of the devices shown can exist to practice the disclosed embodiments. Further, configurations of additional or fewer devices than the devices shown in FIG. 4 can exist to practice the disclosed embodiments. Additionally, the devices shown in FIG. 4 can be combined to allow for fewer devices than shown or can be separated such that more than the three devices exist in a system. It will be appreciated that many various combinations of computing devices can execute the methods and systems disclosed herein. Examples of such computing devices can include other types of medical devices and sensors, infrared cameras/detectors, night vision cameras/detectors, other types of cameras, augmented reality goggles, virtual reality goggles, mixed reality goggle, radio frequency transmitters/receivers, smart phones, personal computers, servers, laptop computers, tablets, blackberries, RFID enabled devices, smart watch or wearables, or any combinations of such devices.

Figure 5:
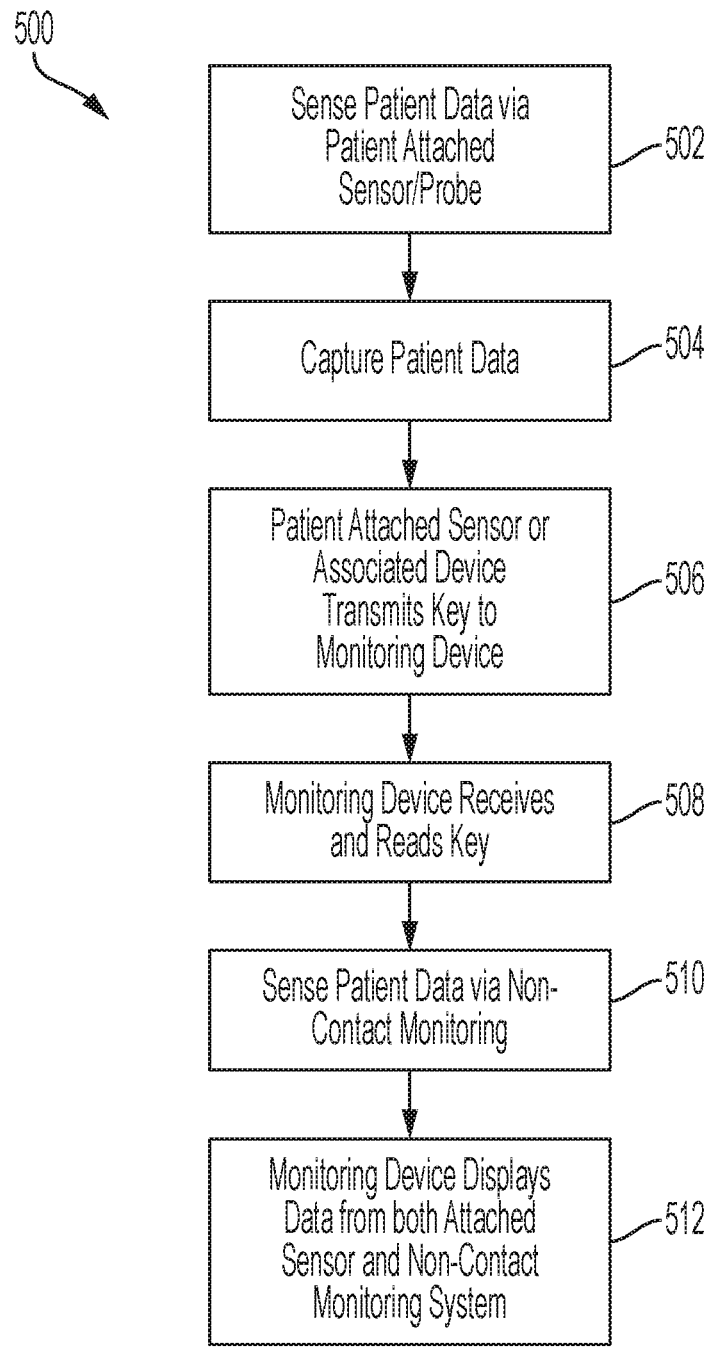
FIG. 5 is a flow diagram illustrating a patient monitoring method for instructing a monitoring device to display attached sensor and NCM data.

FIG. 5 is a flow diagram illustrating a patient monitoring routine 500 for determining and monitoring one or more patient parameters in accordance with various embodiments of the present technology. All or a subset of the steps of the routine 500 can be executed by various components or devices of one or more patient monitoring systems (e.g., the wearable and/or video-based patient monitoring systems described above) and/or users of the system(s) (e.g., a caregiver, a clinician, a patient, etc.).

The routine 500 can begin at block 502 by sensing a data via a patient attached probe (e.g., 112 in FIG. 1). At block 504, the routine 500 can capture first patient data from a sensor in contact with the patient. In some embodiments, the routine 500 can capture patient data using one or more sensors or probes associated with (e.g., contacting) the patient. For example, the routine 500 can use one or more sensors or probes to capture an ECG signal, an EEG signal, a temperature signal, a heart rate signal, a respiratory rate signal, an average temperature signal, and/or one or more other physiological signals relating to the patient. In these and other embodiments, the routine 500 can capture patient data using one or more image capture devices. For example, the routine 500 can use an image capture device to detect a location of the patient, movement of the patient, whether the patient is awake or sleeping, and/or other data relating to the patient.

At block 506, the patient attached sensor or associated device can transmit instructions (e.g., a key) to the monitoring device to instruct the monitoring device to display not just the first patient data from the attached sensor/probe, but also second patient data from the non-contact monitoring (NCM) system. At block 508, the monitoring device receives and reads the key (which may be encrypted) from the patient attached sensor or associated device. As has been discussed above, the instruction can prompt the monitoring device to start receiving data from the NCM system. Such instructions can also activate the NCM system, as well as: allow the monitoring device to include the additional physiological information directly onto a current display screen; allow the device or system to reconfigure a current screen to display the additional physiological information; and/or allow for separate pages to be accessible on the device or system for display of the additional physiological information.

At block 510, the routine 500 can sense/capture second patient data from the video system. For example, the routine 510 can recognize a patient within a field of view (FOV) of one or more image capture devices and/or define one or more regions of interest (ROI's) on the patient. In some embodiments, the routine 510 can recognize the patient by identifying the patient using facial recognition hardware and/or software of the image capture device(s). In these embodiments, the routine 510 can display the name of the patient on a display screen once the routine 510 has identified the patient.

At block 512, the monitoring device (e.g., a MPM device, clinician's tablet, etc.) displays data from both the attached sensor as well as second patient data from the non-contact monitoring system.

Although the steps of the routine 500 are discussed and illustrated in a particular order, the routine 500 illustrated in FIG. 5 is not so limited. In other embodiments, the routine 500 can be performed in a different order. In these and other embodiments, any of the steps of the routine 500 can be performed before, during, and/or after any of the other steps of the routine 500. A person of ordinary skill in the relevant art will readily recognize that the illustrated method can be altered and still remain within these and other embodiments of the present technology.

Figure 6:
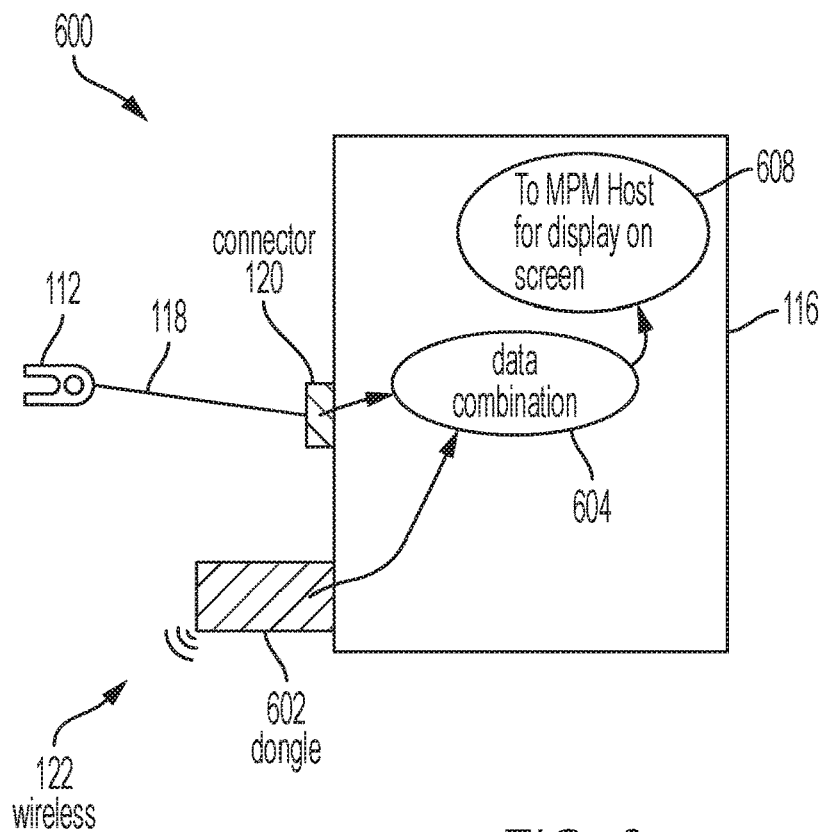
FIG. 6 is a schematic view of a patient monitoring system combining first and second data streams at a monitoring device, configured in accordance with various embodiments of the present technology.

Referring to FIG. 6, optional combination of data streams on a monitoring device, prior to display on a monitoring device screen is illustrated generally at 600. FIG. 6 illustrates a schematic view of a mobile patient monitoring device 116, a probe 112, a wired connector cable 118, a connector 120, a wireless transmission path 122 and a wireless dongle 602. Data combination (shown in the flow portion of the diagram at 604) may occur prior to display on the screen of the MPM 116.

Referring still to FIG. 6, in some embodiments, data streams are switched on and/or combined before display (or before sending to) a monitoring device. FIG. 6 illustrates combination of streams on the monitoring device.

Figure 7:
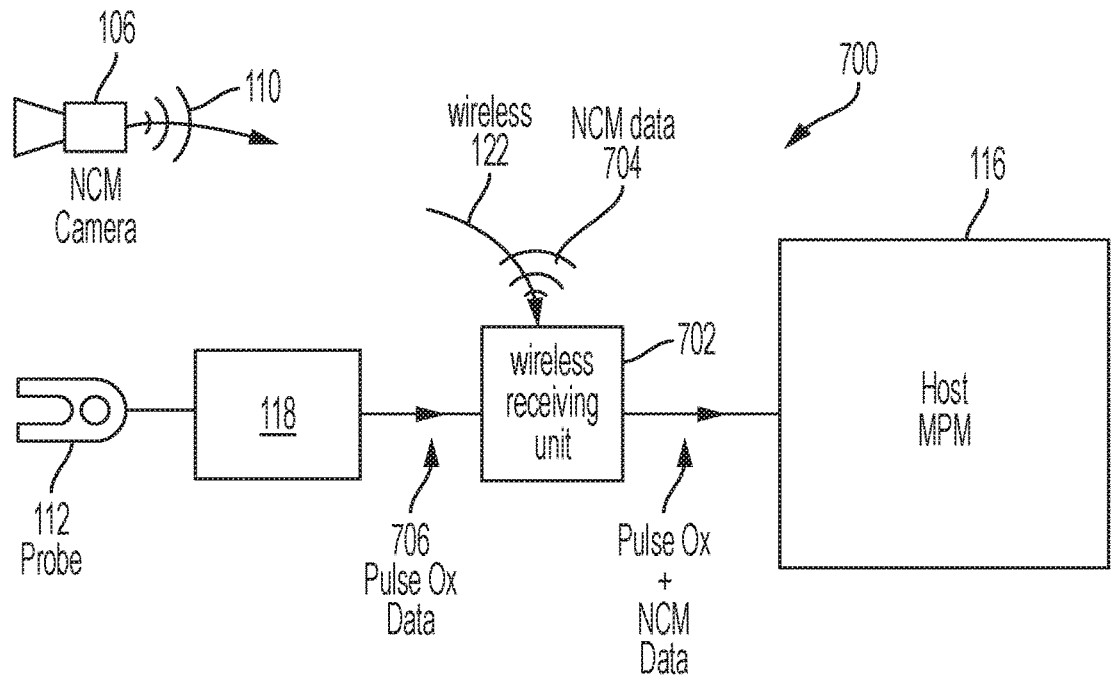
FIG. 7 is a schematic view of a patient monitoring system combining first and second data streams prior to a monitoring device, configured in accordance with various embodiments of the present technology.

FIG. 7 illustrates a schematic view of a system (shown generally at 700), including a monitoring device 116, in combination with a wireless receiving unit 702, with associated wireless transmission path 122, receiving NCM data 704. A physically attached probe, e.g., a pulse oximeter, 112 (though the present disclosure contemplates wireless communication of this data as well) communicates with the wireless receiving unit 702 to transmit pulse oximeter data 706 via a cable 118. FIG. 7 shows a system configured to send a combined stream of digital information to the monitoring device. The wireless receiving unit 702 combines the first (in this case pulse oximeter data) data with the second, NCM data and sends a revised data stream to the monitoring device. In some exemplary embodiments, the revised data stream is formatted, such that existing hardware can use the information without additional hardware or software modifications, while still being able to extract information such as respiration rate, for example, accurately and quickly.

In exemplary embodiments, the wireless receiving unit 702 only sends NCM data if the probe 112 is connected to it, and/or if the probe provides the correct key instructing the wireless receiving unit to use NCM data. Further, in some embodiments, the wireless receiving unit 702 can be configured to only send a subset of the wireless (e.g., NCM data) streamed to it. For example, the wireless receiving unit could be configured only to send out respiratory rate, combined with pulse oximeter parameters. In other embodiments, it could only stream out apnea detection flags with pulse oximetry parameters, only stream out patient posture information, etc. Accordingly, some embodiments provide customized or customizable wireless receiving units according to different possible desired parameters handled by the wireless receiving units.

In some embodiments, the data streams referred to above may include numerical values of a physiological parameter (e.g., heart rate, respiratory rate), a flag indicating a state (e.g., an apnea flag, a sensor-off flag, etc.), a physiological waveform (e.g., PPG, ECG, EEG, $CO_2$), a video stream (e.g. from an RGB or depth camera), etc.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A patient monitoring system, comprising:
    a first sensor in contact with a patient, the first sensor providing first physiological data related to the patient to determine one or more patient parameters;
    a non-contact video monitoring system programmed to capture second physiological data related to the patient, wherein the video monitoring system includes a camera;
    a monitoring device; and
    a wireless receiver configured to activate the non-contact video monitoring system and combine the first and second physiological data and pass the combined data to the monitoring device;
    wherein the monitoring device is configured to receive the combined data and display said first physiological data and the second physiological data, wherein the wireless receiver instructs said monitoring device to display said second physiological data.

2. The patient monitoring system of claim 1, wherein the wireless receiver is configured to activate the non-contact video monitoring system based upon the first physiological data and to instruct the monitoring device to display the second physiological data.

3. The patient monitoring system of claim 1, wherein the wireless receiver uses the non-contact video monitoring data based upon instructions from an encrypted key.

4. The patient monitoring system of claim 1, wherein the non-contact video monitoring system is programmed to:
 define one or more regions of interest (ROI's) on a patient;
 capture the second physiological data related to the patient, wherein the second physiological data includes two or more images of the ROI's; and
 measure changes in depths of the ROI's across the two or more images of the ROI's.

5. The patient monitoring system of claim 1, wherein the camera includes a depth sensing camera, an RGB camera, and/or an infrared camera.

6. The patient monitoring system of claim 1, wherein the instructions are configured to: allow the monitoring device to include the second physiological data directly onto a current display screen; allow the monitoring device to reconfigure a current screen to display the second physiological data; and/or allow for separate pages to be accessible on the monitoring device for display of the second physiological data.

7. The patient monitoring system of claim 1, wherein only predetermined subsets of data from one or both of first and second physiological data are displayed at said monitoring device.

8. A method for patient monitoring comprising:
 providing a first sensor in contact with a patient, the first sensor providing first physiological data to determine one or more patient parameters;
 providing a non-contact video monitoring system programmed to capture second physiological data related to the patient, wherein the video monitoring system includes a camera;
 providing a wireless receiver configured to activate the non-contact video monitoring system and combine the first and second physiological data and pass the combined data to a monitoring device; and
 passing the combined data to a the monitoring device and displaying the first and second physiological data on the monitoring device.

9. The method of claim 8, wherein the wireless receiver is configured to activate the non-contact video monitoring system based upon the first physiological data and to instruct the monitoring device to display the second physiological data.

10. The method of claim 8, wherein the wireless receiver uses the non-contact video monitoring data based upon instructions from an encrypted key.

11. The method of claim 8, wherein the non-contact video monitoring system is programmed to:
 define one or more regions of interest (ROI's) on a patient;
 capture the second physiological data related to the patient, wherein the second physiological data includes two or more images of the ROI's; and
 measure changes in depths of the ROI's across the two or more images of the ROI's.

12. The method of claim 8, wherein the camera includes a depth sensing camera, an RGB camera, and/or an infrared camera.

13. The method of claim 8, wherein instructions provided to the monitoring device are configured to: allow the monitoring device to include the second physiological data directly onto a current display screen; allow the monitoring device to reconfigure a current screen to display the second physiological data; and/or allow for separate pages to be accessible on the monitoring device for display of the second physiological data.

14. The method of claim 8, wherein only predetermined subsets of data from one or both of first and second physiological data are displayed at said monitoring device.

15. The patient monitoring system of claim 1, wherein the second physiological data is transmitted wirelessly to the wireless receiver; and wherein the wireless receiver is configured to only send a subset of second physiological data, along with first physiological data to the monitoring device.

16. The method of claim 8, wherein the second physiological data is transmitted wirelessly to the wireless receiver; and wherein the wireless receiver is configured to only send a subset of second physiological data, along with first physiological data to the monitoring device.

* * * * *